United States Patent [19]

Harandi et al.

[11] Patent Number: 5,030,783
[45] Date of Patent: Jul. 9, 1991

[54] ENDOTHERMIC HYDROCARBON UPGRADING PROCESS

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 569,309

[22] Filed: Aug. 20, 1990

Related U.S. Application Data

[62] Division of Ser. No. 297,785, Jan. 17, 1989, Pat. No. 4,950,691.

[51] Int. Cl.⁵ ............................................. C07C 1/04
[52] U.S. Cl. ..................................... 585/322; 585/324; 585/408; 585/638; 518/702; 518/703
[58] Field of Search ............... 518/702, 703; 585/322, 585/324, 408, 638, 733

[56] References Cited

U.S. PATENT DOCUMENTS

| | | | |
|---|---|---|---|
| 3,756,942 | 9/1973 | Cattanach | 208/137 |
| 3,759,821 | 9/1973 | Brennan et al. | 208/93 |
| 3,760,024 | 9/1973 | Cattanach | 260/673 |
| 4,016,218 | 4/1977 | Haag et al. | 260/671 R |
| 4,076,761 | 2/1978 | Chang et al. | 585/324 |
| 4,159,995 | 7/1979 | Haag et al. | 585/322 |
| 4,207,250 | 6/1980 | Butter et al. | 252/455 Z |
| 4,255,349 | 3/1981 | Butter et al. | 252/455 Z |
| 4,293,446 | 10/1981 | Butter et al. | 252/455 Z |
| 4,617,288 | 10/1986 | Bell et al. | 502/331 |
| 4,686,312 | 8/1987 | Chu et al. | 585/315 |
| 4,686,313 | 8/1987 | Bell et al. | 585/327 |
| 4,696,732 | 9/1987 | Angevine et al. | 201/111 |
| 4,751,338 | 6/1988 | Tabak et al. | 585/415 |
| 4,950,691 | 8/1990 | Harandi et al. | 518/702 |

Primary Examiner—Curtis R. Davis
Assistant Examiner—William C. Diemler
Attorney, Agent, or Firm—Alexander J. McKillop; Charles J. Speciale; Robert B. Furr, Jr.

[57] ABSTRACT

A process is disclosed for the conversion of an aliphatic feedstream in which an oxygen-deficient flue gas is used to directly transfer heat to the primary conversion reaction. Hydrogen, carbon monoxide and carbon dioxide from the primary conversion reactor effluent are converted to methanol or Fischer-Tropsch liquid and may be recycled to the primary conversion reactor. Preferred primary conversion reactions include dehydrogenation and aromatization of aliphatics.

16 Claims, 1 Drawing Sheet

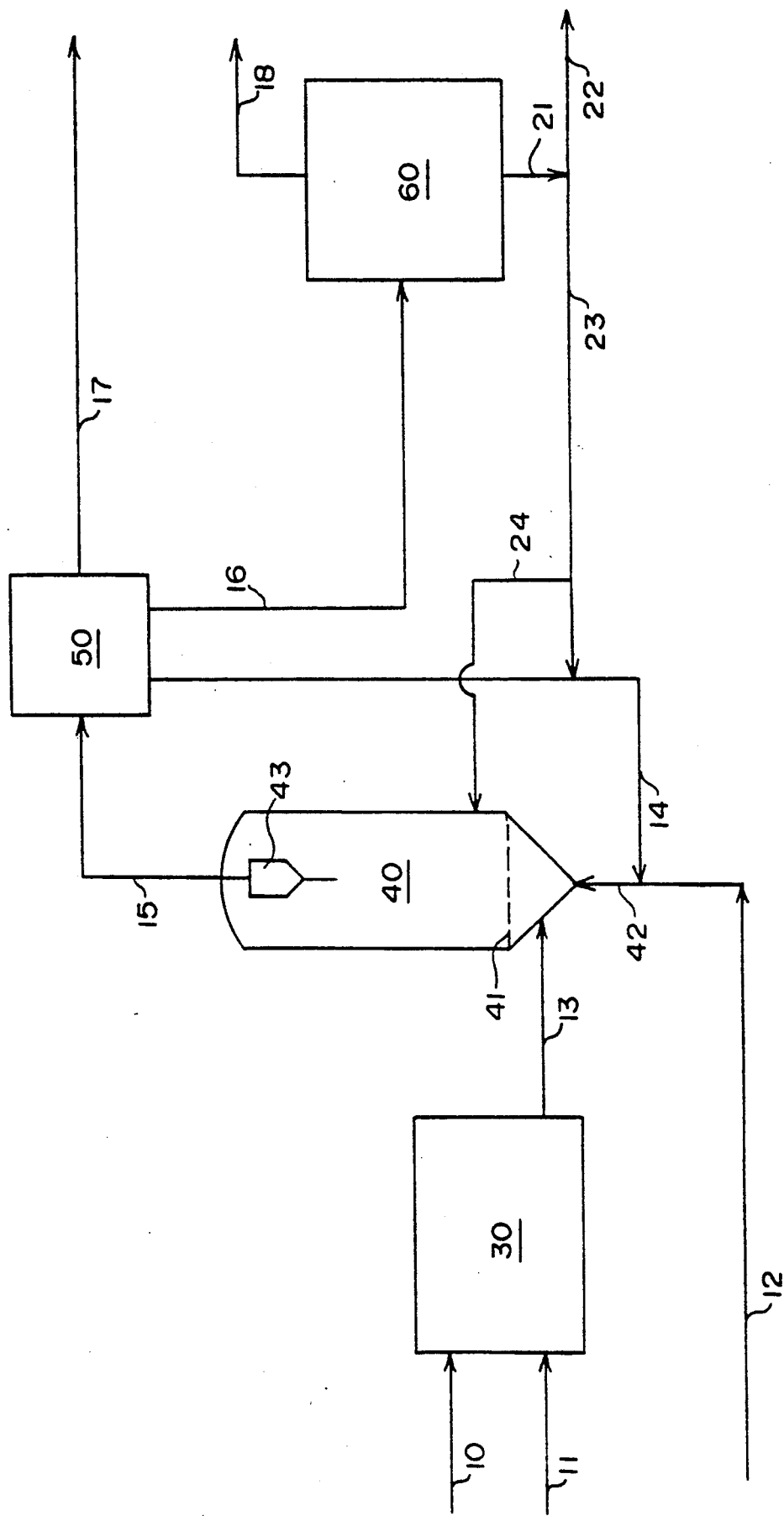

ENDOTHERMIC HYDROCARBON UPGRADING PROCESS

CROSS-REFERENCE TO RELATED APPLICATIONS

This is a division of copending U.S. application Ser. No. 297,785, filed Jan. 17, 1989 now U.S. Pat. No. 4,950,691.

BACKGROUND OF THE INVENTION

This invention relates to an improved process in which aliphatic hydrocarbons are upgraded in a high-temperature endothermic conversion process. In particular, the invention provides a method for directly transferring heat to a fluid-bed aromatization reaction zone while also increasing the yield of valuable products.

The problem of transferring heat to high-temperature fluid bed endothermic hydrocarbon upgrading processes has been an obstacle to their commercial development. Methods known in the art for transferring heat to the fluid-bed reaction zone include preheating the catalyst or positioning a heat exchanger in the fluidized catalyst bed.

To heat the reaction zone with preheated catalyst, the catalyst typically enters the reaction zone at a temperature above about 870° C. (1600° F.). Heating the catalyst to such temperature generally requires passing the catalyst through a combustion zone which, due to the presence of water vapor at high temperatures, causes permanent steam deactivation of the catalyst. On the other hand, the installation of a heat exchanger increases capital costs due not only to the expense associated with an alloy heat exchange bundle but also to expenses resulting from enlarging the reactor shell to maintain a given reaction zone volume. Moreover, operation of such a design is more costly due both to maintenance expenses as well as to increased energy consumption associated with relatively inefficient indirect heat transfer.

Further, direct heat exchange with inert solid particles requires that the particles be heated, transported to the reaction zone, mixed with the reactants and then separated from the products. Thus, it can be seen that a method providing the benefits of direct heat transfer to a high temperature endothermic fluid-bed reaction zone without the materials handling problems associated with solid particles would enhance the commercial viability of such conversion processes.

SUMMARY OF THE INVENTION

The process of the present invention provides the benefits of efficient direct heat transfer while avoiding the materials handling problems arising from the use of circulating particles. The process burns a fuel, preferably a hydrogen-deficient fuel, to form a flue gas having a very low oxygen content. The fuel is most preferably coke or charcoal low in metal, sulfur and nitrogen compounds. Hot flue gas is then charged to the reaction zone together with an aliphatic hydrocarbon feed where the aliphatic feedstream reacts endothermically in the presence of catalyst to yield an upgraded product. The reaction zone is preferably a fluid bed reaction zone. Depending on the choice of catalyst and the process conditions, the upgraded product may comprise olefins, aromatics or a mixture of both. Two conversion reactions particularly preferred for use with the process of the invention include dehydrogenation and aromatization of aliphatic feedstreams.

The hot flue gas transfers heat directly to the reaction zone. While the hydrogen, carbon monoxide and carbon dioxide which are the predominant components of the flue gas may react to a degree, a substantial portion of the flue gas passes through the reaction zone essentially inert. This unreacted flue gas is separated and charged to a secondary conversion process, preferably a Fischer-Tropsch or methanol synthesis process. The Fischer-Tropsch synthesis process yields an olefinic product stream.

In a preferred embodiment of the invention, the reaction zone contains an aromatization catalyst and the Fischer-Tropsch liquid or methanol product from the secondary conversion process is recycled to the aromatization reaction zone. As is the case in all embodiments of the invention, the preferred embodiment provides highly efficient direct heat transfer to the fluid-bed reaction zone as well as increased product yield by converting flue gas to useful products. But the preferred embodiment provides still further benefits by recycling the secondary conversion product stream to the aromatization reactor. Both methanol and the olefinic Fischer-Tropsch product react exothermically at high temperature in the presence of an aromatization catalyst such as a medium-pore zeolite. Thus, not only is the secondary conversion product stream upgraded to even more valuable aromatics, it also contributes thermal energy at high temperatures to the aromatization reaction zone.

Recognizing from the previous discussion that heat transfer to high temperature strongly endothermic fluid-bed reaction zones is a critical obstacle to be overcome in commercializing such processes, the value of the present inventive process may now be fully appreciated. In the preferred embodiment, the inventive process not only transfers heat directly to the aromatization reaction zone, it further recycles a secondary conversion product stream which reacts exothermically in the aromatization reaction zone not only to increase aromatics yield but also to transfer additional heat to the reaction zone.

The process of the present invention upgrades aliphatic hydrocarbons to olefinic and aromatic hydrocarbons by the steps of burning a hydrogen-deficient fuel under oxygen-deficient conditions to evolve a hot flue gas containing at most a small amount of oxygen, maintaining a first catalyst in a first reaction zone, directly transferring thermal energy from the hot flue gas to the first reaction zone by flowing the hot flue gas through the first reaction zone, contacting an aliphatic hydrocarbon feedstream with the first catalyst under primary conversion conditions in the reaction zone, withdrawing a reactor effluent stream from the first reaction zone, separating the reactor effluent stream into an aromatics-rich product stream, a secondary conversion feedstream comprising $H_2$, CO and $CO_2$, and a recycle stream comprising $C_3$–$C_5$ aliphatics, and contacting the secondary conversion feedstream with a second solid catalyst under conversion conditions to evolve a secondary conversion product stream. The process may also include recycling the $C_3$–$C_5$ aliphatic stream to the first reaction zone. In a preferred embodiment, the process further comprises charging the secondary conversion product stream to the first reaction zone. It is to be understood, however, that while recycling the secondary conversion is advantageous when the first reaction zone contains an aromatization catalyst, such recycling would be undesirable if the first reaction zone contains a dehydrogenation catalyst.

The process may still further comprise reacting the secondary conversion feedstream in a second reaction zone to form a secondary conversion product comprising methanol. Alternatively, the process may comprise reacting the secondary conversion feedstream in the presence of a Fischer-Tropsch catalyst to form a secondary conversion product comprising olefinic $C_5+$ gasoline.

DESCRIPTION OF THE DRAWING

The FIGURE is a simplified schematic diagram illustrating the process of the present invention.

DETAILED DESCRIPTION

The process of the present invention uses flue gas from the controlled combustion of a fuel, preferably a hydrogen-deficient fuel, to heat an endothermic reaction zone. A portion of the flue gas passes through the reaction zone essentially inert and is separated from reaction products downstream from the reaction zone in a product separator. Some of the flue gas, however, reacts exothermically with hydrogen or hydrocarbons in the primary reaction stage. The secondary conversion feedstream comprising controlled amounts of $H_2$, CO, and $CO_2$ is then reacted to form a secondary conversion product. In a first embodiment, the secondary conversion product comprises methanol. In a second embodiment, the secondary conversion product comprises a Fischer-Tropsch olefinic hydrocarbon mixture. In both embodiments, the optionally recycled material reacts exothermically, reducing the net heat input required to the primary reaction stage. Further, the present process increases valuable product yield over past processes by deriving both heat of reaction as well as incremental product yield from a fuel source which, in previous processes, provided only heat of reaction.

COMBUSTION OF FUEL

The present process generates hot flue gas from the controlled combustion of a fuel, preferably a hydrogen-deficient fuel. Air or oxygen-containing inert gas, preferably relatively pure oxygen, is charged to a combustion chamber at a controlled rate to maintain the desired ratio of hydrogen to carbon monoxide and carbon dioxide at the outlet of the downstream endothermic fluid-bed reaction zone. Alternatively, oxygen flow may be indexed to the first reaction zone temperature to generate flue gas at flowrates and temperatures sufficient to supply the endothermic heat of reaction to the fluid-bed reaction zone. As can be seen by one skilled in the art, increasing oxygen charge shifts the $CO/CO_2$ balance toward $CO_2$ while decreasing oxygen charge shifts the balance toward CO. Hydrogen is evolved in the downstream endothermic reaction zone while a significant portion of the flue gas including carbon monoxide flows through the endothermic reaction zone unreacted. Thus the $H_2:CO+CO_2$ ratio at the endothermic reaction zone outlet may be controlled by adjusting oxygen and fuel charge rates to the combustion chamber.

The preferred fuel for firing in the combustion chamber is a hydrogen-deficient fuel such as charcoal or coke. Hydrogen-deficient liquid fuels such as petroleum oil residua may also be used.

Water in the flue gas promotes permanent steam deactivation of the downstream catalyst and is highly undesirable. Hydrogen-deficient fuels are therefore strongly preferred. Similarly, low sulfur and nitrogen fuels are preferred as both elements tend to form corrosive compounds under combustion zone conditions.

AROMATIZATION PROCESS

Hydrocarbon upgrading reactions compatible with the process of the present invention include the conversion of aliphatic hydrocarbons to aromatic hydrocarbons. The article "M2 Forming-A Process for Aromatization of Light Hydrocarbons" by N. Y. Chen and T. Y. Yan, *Ind. Eng. Chem. Process Des. Dev.* 25, 151-155 (1986), surveys developments in the area of light aliphatics aromatization and discloses a theoretical mechanism for the reactions. The text of the Chen et al. article is incorporated by reference as if set forth at length herein. The following representative U.S. patents detail the feed compositions and process conditions for these reactions. Aromatization process conditions are summarized in Table 1.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2-C_4$ paraffins and/or olefins with a crystalline aluminosilicate, e.g. ZSM-5.

Details of the operation of a fluid-bed aromatization reactor are taught in U.S. Pat. No. 4,751,338 to Tabak et al., incorporated by reference as if set forth at length herein.

Hydrocarbon feedstocks which can be converted according to the present process include various refinery streams including coker gasoline, light FCC gasoline, $C_5-C_7$ fractions of straight run naphthas and pyrolysis gasoline, as well as raffinates from a hydrocarbon mixture which has had aromatics removed by a solvent extraction treatment. Examples of such solvent extraction treatments are described in *Kirk-Othmer Encyclopedia of Chemical Technology*, Third Edition, Vol. 9, 706-709 (1980). A particular hydrocarbon feedstock derived from such a solvent extraction treatment is a Udex raffinate. Propane-rich refinery streams commonly referred to as LPG are particularly preferred for upgrading to aromatics and olefins in the process of the present invention.

TABLE 1

| WHSV | Broad range: | 0.3-300 hr$^{-1}$ |
|---|---|---|
| | Preferred range: | 1-10 hr$^{-1}$ |
| OPERATING PRESSURE | Broad: | 170-2170 kPa (10-300 psig) |
| | Preferred: | 310-790 kPa (30-100 psig) |
| OPERATING TEMPERATURE | Broad: | 480-820° C. (900-1500° F.) |
| | Preferred: | 560-620° C. |

TABLE 1-continued
(1050-1150° F.)

The reaction severity conditions can be controlled to optimize yield of $C_6$–$C_8$ BTX (benzene, toluene and xylene) hydrocarbons. It is understood that aromatics and light olefin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) ca be maintained from high activity values greater than 40 to significantly lower values under steady state operation by controlling fresh catalyst makeup as well as catalyst deaetivation and regeneration rates to provide inventory) below 40, preferably about 2 to 20.

Aromatization Catalysts

The members of the class of zeolites useful herein for the conversion of aliphatic to aromatic hydrocarbons have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. No. Re. 29,948 (highly siliceous ZSM-5); U.S. Pat. Nos. Re. 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

In addition to those zeolites having effective pore sizes ranging from about 5 to about 8 Angstroms, other zeolites such as Zeolite Beta may be useful in the conversion of aliphatic hydrocarbons. Zeolite Beta is described in U.S. Pat. No. 3,308,069 which is incorporated by reference as if set forth at length herein.

Dehydrogenation Catalysts

Paraffin dehydrogenation catalysts also include oxides and sulfides of Groups IVA, VA, VIA, VIIA and VIIIA and mixtures thereof on an inert support such as alumina or silica-alumina. Thus, dehydrogenation may be promoted by sulfides and oxides of titanium, zirconium, vanadium, mobium, tantalum, chromium, molybdenum, tungsten and mixtures thereof. Oxides of chromium alone or in conjunction with other catalytically active species have been shown to be particularly useful in dehydrogenation. Other catalytically active compounds include sulfides and oxides of manganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having dehydrogenation activity. Platinum has been found to be particularly useful for promoting dehydrogenation over zeolite catalysts.

Methanol Synthesis

In a first embodiment of the present invention, carbon monoxide and carbon dioxide from the combustion of fuel and hydrogen derived from dehydrogenation of paraffins in the aromatization reactor are reacted to form methanol.

Methanol has been produced commercially by synthesis from pressurized mixtures of hydrogen, carbon monoxide and carbon dioxide gases in the presence of heterogeneous metallic catalysts. The initial high pressure processes using zinc oxide-chromium oxide catalyst were later replaced by medium and low pressure processes employing copper oxide-zinc oxide catalysts even though these catalysts were sufficiently sensitive to poisons as to require careful purification of the feed streams. The catalyst may be supported on metallic copper in order to prevent local overheating in the catalyst bed.

The use of aluminum oxide as an additional component for the copper oxide-zinc oxide catalysts is known and is described, for example, in "Synthesis of Methanol from Carbon Monoxide and Hydrogen", *Industrial and Engineering Chemistry* 20, 285-290 (1928). U.S. Pat. No. 4,111,847 also describes the use of alumina and other materials such as zirconia, titania, silica, calcia or magnesia as thermal stabilizers for copper oxide zinc oxide catalysts. British Patent 1,159,035 describes similar catalyst systems based on the oxides of copper and zinc together with alumina, titania, zirconia, ceria or thoria, optionally with the addition of chromia. Catalyst systems of this kind are said to be capable of operation for long periods of time at low pressures and temperatures, while producing only small amounts of organic impurities. U.S. Pat. No. 3,790,505 also describes catalysts of this kind.

Chromium oxide has also been proposed for use in combination with zinc oxide and copper oxide low temperature methanol synthesis of the kind disclosed in U.S. Pat. No. 3,326,956, even though the catalysts of this kind have poor resistance to aging and are relatively sensitive to poisons, as described in the article by Natta in *Catalysis,* Vol. III, (1955), and in DE-AS No. 1300538. Chromia is also proposed as a substitute for alumina in copper oxide-zinc oxide based system in U.S. Pat. No. 3,850,850.

A four component catalyst for synthesizing alcohols from synthesis gas is proposed in U.S. Pat. No. 4,122,110; the catalyst comprises components derived from copper, cobalt, a third metal (Cr, Fe, V or Mn) and an alkali metal, preferably lithium, sodium or potassium. Other components may also be present e.g. a zinc component. The selectivity of this catalyst to the production of alcohols is said to be high with practically no hydrocarbons being produced.

The above-cited patents and publications are incorporated by reference as if set forth at length herein.

Generally speaking, this process requires that the stoichiometry of the synthesis gas be adjusted so that there are about two moles of hydrogen per mole of carbon monoxide. In the present process, such control is accomplished by adjusting the rates of oxygen and fuel addition to the combustion chamber.

Fischer-Tropsch Synthesis

In a second embodiment of the present invention, carbon monoxide and carbon dioxide from the combustion of fuel and hydrogen derived from dehydrogenation of paraffins in the aromatization reactor are reacted to form an olefinic hydrocarbon stream.

Processes for the conversion of coal and other hydrocarbons, such as natural gas, to a gaseous mixture consisting essentially of hydrogen and carbon monoxide and/or dioxide are well known. Those of major importance depend either on the partial combustion of the fuel with an oxygen-containing gas or on the high temperature reaction of the fuel with steam, or on a combination of these two reactions. An excellent summary of synthetic fuel manufacture is given in *Kirk-Othmer Encyclopedia of Chemical Technology,* Third Edition, Vol. 2, 447-489 (1980).

It is also well known that synthesis gas will undergo conversion to reduction products of carbon monoxide, such as hydrocarbons, at from about 300° F. to about 850° F., under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. Catalysts that have been studied for this and related processes include those based on iron, cobalt, nickel, rutherium, thorium, rhodium and osmium, or their oxides. For example, U.S. Pat. Nos. 4,293,446; 4,255,349; and 4,207,250, all to Butter et al., teach processes for the conversion of synthesis gas in the presence of iron-containing catalysts. U.S. Pat. No. 4,207,250 also to Butter et al. teaches a process for the conversion of synthesis gas in the presence of a cobalt containing catalyst. Additionally, U.S. Pat. Nos. 4,617,288 and 4,686,313 to Bell et al. teach a Fischer-Tropsch conversion process and a low-nitrogen iron-containing catalyst useful therein. The above-listed patents and publications are incorporated by reference as if set forth at length herein.

DESCRIPTION OF THE PREFERRED EMBODIMENT

The following preferred embodiments detail the process of the invention wherein the fluid-bed reaction zone contains an aromatization catalyst.

First Embodiment

In a first embodiment of the present invention, an aliphatic feedstream is upgraded to a predominantly aromatic product stream. Hot flue gas rich in carbon monoxide and carbon dioxide from the combustion chamber flows through the aromatization reactor providing the necessary heat of reaction by direct heat transfer. The flue gas may partially and exothermically react in the aromatization reaction zone, but a significant portion flows through unreacted and is subsequently separated in admixture with hydrogen from the predominately aromatic product stream. The separated carbon monoxide, carbon dioxide and hydrogen which is evolved in the aromatization reaction are then converted to methanol in a methanol conversion unit and recycled to the aromatization reaction zone or withdrawn as product. Preferably, the methanol is recycled to the aromatization reaction zone.

Referring now to the FIGURE, a hydrogen-deficient fuel such as charcoal, coke, or residual oil is charged to a combustion chamber 30 through line 10. Air or an oxygen-rich mixture of inert gases preferably relatively pure oxygen flows through line 11 to combustion chamber 30 at a rate controlled by the $H_2:CO+CO_2$ molar ratio at the outlet of the aromatization reactor as described above. Flue gas temperature at the combustor outlet may be controlled by indirect heat exchange to preheat reactor feed or to generate steam. The $H_2:CO+CO_2$ ratio of the aromatization reactor outlet should be maintained between about 0.1 and 20, preferably between 1 and 3.

Hot flue gas at a temperature between 650° and 1370° C. (1200° and 2500° F.), typically at least 870° C. (1600° F.) flows from combustion chamber 30 through line 13 to aromatization reactor 40 and enters the reactor at a point below the vapor distributor 41.

Preheated aliphatic feed from line 12 enters reactor charge line 42 at a temperature preferably between about 454° and 538° C. (850° and 1000° F.) and is joined by methanol and recycled unreacted $C_3$-$C_5$ aliphatics from line 14. The combined charge is fed to the bottom of aromatization reactor to where it enters a turbulent fluid-bed reaction zone. Methanol may optionally be charged to a secondary injection point in the aromatization reactor above the distributor grid through line 24.

Entrained catalyst fines are separated from the reaction product mixture in one or more cyclone separators 43 and the reaction product mixture is withdrawn from aromatization reactor 40 through line 15. Sintered metal filters may optionally be installed in line 15 to remove catalyst fines from the reactor effluent stream.

The reactor effluent stream is then charged through line 15 to product recovery section 50 which comprises at least one fractionation tower. Finished product comprising $C_6+$ aromatics is routed to product storage via line 17 while $C_3$-$C_5$ aliphatics are preferably recycled to reactor charge line 42 via line 14. A stream containing hydrogen, carbon monoxide and carbon dioxide is charged through line 16 to conversion plant 60 which is, in the first embodiment, a methanol conversion process from which methanol is withdrawn via line 21. Reactor configuration, catalysts and process conditions for the methanol coversion process are described in the above-cited references. Flow in line 21 is split between recycle line 23, which recycles methanol to aromatization reactor 40 through lines 14 or 24, and line 22 which optionally routes methanol to product storage. Unconverted $C_3-$ gas flows to a fuel gas header (not shown) through line 18.

Second Embodiment

In a second embodiment of the present invention, an aliphatic feedstream is upgraded as in the first embodiment except that flue gas from the combustion chamber together with hydrogen from the aromatization reactor react in the presence of a Fischer-Tropsch catalyst to form an aliphatic hydrocarbon recycle stream.

Referring to the FIGURE, a hydrogen-deficient fuel as described in the first embodiment is charged to combustion chamber 30. As in the first embodiment, air or oxygen-containing inert gas mixture is fed to combustion chamber 30 through line 11. The second embodiment, however, includes a Fischer-Tropsch synthesis rather than methanol synthesis. Oxygen charge to the combustion chamber 30 should therefore be maintained at a rate sufficient to provide a $H_2:CO+CO_2$ molar ratio at the aromatization reactor outlet of between about 0.1 and 20, preferably between 1 and 3.

Hot flue gas at a temperature between 650° and 1370° C. (1200° and 2500° F.), typically at least 870° C. (1600° F.) flows from combustion chamber 30 through line 13 to aromatization reactor 40 as in the first embodiment.

Preheated aliphatic feed from line 12 enters reactor charge line 42 as described above but in the second embodiment is mixed with a Fischer-Tropsch aliphatic hydrocarbon stream and unreacted aliphatic feed from line 14. The combined charge is fed to the bottom of aromatization reactor 40 as described above. Alternatively, the Fischer-Tropsch hydrocarbon stream may be charged to a secondary injection point in the aromatization reactor above the distributor grid 41.

Entrained catalyst and the reaction product mixture are separated as described above and the reaction product mixture is charged to product recovery section 50 which contains at least one fractionation tower. Finished product comprising $C_6+$ aromatics is sent to product storage via line 17 while $C_3$-$C_5$ aliphatics are preferably recycled to reactor charge line 42 via line 14. A stream containing hydrogen, carbon monoxide and carbon dioxide is charged through line 16 to conversion plant 60, which is, in the second embodiment, a Fischer-Tropsch synthesis process. The hydrogen, carbon monoxide and carbon dioxide react in the Fischer-Tropsch synthesis process to form an aliphatic gas, which flows through line 18 to a light gas recovery section (not shown), and an olefinic liquid stream which leaves conversion plant 60 via line 21. Olefinic liquid flows through line 21 and is divided between lines 22 and 23. Line 23 recycles olefinic liquid through lines 14 and 24 to aromatization reactor 40. A portion of the olefinic liquid may optionally be sent to storage via line 22.

Changes and modifications in the specifically described embodiments can be carried out without departing from the scope of the invention which is intended to be limited only by the scope of the appended claims.

What is claimed is

1. A process for upgrading aliphatic hydrocarbons to aromatic hydrocarbons comprising the steps of:
    (a) burning a hydrogen-deficient fuel under oxygen-deficient conditions to evolve a hot flue gas containing essentially no oxygen;
    (b) providing an aromatization reaction zone containing a zeolite catalyst;
    (c) directly transferring a quantity of thermal energy from said hot flue gas to said aromatization reaction zone by flowing hot flue gas through said aromatization reaction zone, said quantity of thermal energy being sufficient to supply the endothermic heat of reaction to aromatize at least a portion of said aliphatic feedstream;
    (d) contacting an aliphatic hydrocarbon feedstream with said zeolite catalyst under primary conversion conditions in said aromatization reaction zone to evolve an aromatization reaction zone effluent stream containing aromatics;
    (e) withdrawing said aromatization reaction zone effluent stream from said aromatization reaction zone;
    (f) separating said aromatization reaction zone effluent stream into a product stream, a secondary conversion feedstream comprising CO, $CO_2$, and $H_2$ and a stream containing $C_3$-$C_5$ aliphatics; and
    (g) charging said secondary conversion feedstream of step (f) to a hydrocarbon synthesis reaction zone containing a catalyst comprising a metal oxide on an inert support under Fischer-Tropsch synthesis conditions to convert at least a portion of said secondary conversion feedstream to a mixture of aliphatic liquid hydrocarbons.

2. The process of claim 1 further comprising recycling said $C_3$-$C_5$ aliphatics of step (f) to said aromatization reaction zone to upgrade a portion of said $C_3$-$C_5$ aliphatics to aromatics.

3. The process of claim 1 wherein said zeolite has a Constraint Index of from about 1 to about 12.

4. The process of claim 3 wherein said zeolite has the structure of at least one selected from the group consisting of ZSM-5, ZSM-11, ZSM-22, ZSM-23, ZSM-35 and ZSM-48.

5. The process of claim 4 wherein said zeolite contains gallium.

6. The process of claim 1 further comprising maintaining said aromatization reaction zone under conditions including WHSV from 0.3 to 300 $hr^{-1}$, pressures from about 170 to 2170 kPa, and temperatures from 540° to 820° C.

7. The process of claim 1 further comprising maintaining said aromatization reaction zone under conditions including WHSV from 0.3 to 10 hr$^{-1}$, pressures from about 310 to 790 kPa, and temperatures from 560° to 620° C.

8. A process for upgrading aliphatic hydrocarbons comprising the steps of:
 (a) burning a hydrogen-deficient fuel under oxygen-deficient conditions to evolve a hot flue gas containing essentially no oxygen;
 (b) providing a dehydrogenation catalyst in a first reaction zone;
 (c) directly transferring thermal energy from said hot flue gas to said first reaction zone by flowing said hot flue gas through said first reaction zone;
 (d) contacting an aliphatic hydrocarbon feedstream with said dehydrogenation catalyst under primary conversion conditions in said first reaction zone to convert said aliphatic hydrocarbon feedstream to a reactor effluent stream;
 (e) withdrawing said reactor effluent stream from said first reaction zone;
 (f) separating said reactor effluent stream into a product stream, a secondary conversion feedstream comprising CO, $CO_2$, and $H_2$ and a recycle stream comprising $C_3$–$C_5$ aliphatics; and
 (g) contacting said secondary conversion feedstream with a second catalyst under secondary conversion conditions to convert said secondary conversion feedstream to a secondary conversion product stream.

9. The process of claim 8 further comprising recycling said $C_3$–$C_5$ recycle stream to said first reaction zone of step (b).

10. The process of claim 8 wherein said dehydrogenation catalyst comprises a metal oxide on an inert support.

11. The process of claim 8 wherein said oxygen-deficient burning conditions of step (a) comprise temperatures of at least 760° C.

12. The process of claim 8 wherein said primary conversion conditions comprise WHSV between 0.3 and 300 hr$^{-1}$, pressures between 170 and 2170 kPa, and temperatures between 540° and 820° C.

13. The process of claim 12 wherein said primary conversion conditions further comprise WHSV between 0.1 and 10 hr$^{-1}$, pressures between 310 and 790 kPa, and temperatures between 560° and 620° C.

14. The process of claim 8 wherein said second catalyst comprises a metal oxide on an inert support and said secondary conversion conditions comprise Fischer-Tropsch synthesis conditions for converting a mixture comprising hydrogen and carbon monoxide to a mixture of aliphatic liquid hydrocarbons.

15. The process of claim 8 wherein said second catalyst comprises a methanol synthesis catalyst.

16. The process of claim 8 wherein said second catalyst comprises a Fischer-Tropsch catalyst.

* * * * *